(12) United States Patent
Schreiber

(10) Patent No.: US 9,903,115 B2
(45) Date of Patent: Feb. 27, 2018

(54) AIRFRAME SYSTEM AND METHOD OF CONTROLLING AIRFLOW

(71) Applicant: Kevin Joseph Schreiber, Milwaukie, OR (US)

(72) Inventor: Kevin Joseph Schreiber, Happy Valley, OR (US)

(73) Assignee: SLD Technology, Inc., Portland, OR (US)

( * ) Notice: Subject to any disclaimer, the term of this patent is extended or adjusted under 35 U.S.C. 154(b) by 0 days.

(21) Appl. No.: 15/288,232

(22) Filed: Oct. 7, 2016

(65) Prior Publication Data
US 2017/0101778 A1    Apr. 13, 2017

Related U.S. Application Data

(60) Provisional application No. 62/238,601, filed on Oct. 7, 2015.

(51) Int. Cl.
| | |
|---|---|
| *E04B 9/02* | (2006.01) |
| *E04B 9/00* | (2006.01) |
| *A61B 90/35* | (2016.01) |
| *A61B 90/40* | (2016.01) |
| *A61G 13/10* | (2006.01) |

(52) U.S. Cl.
CPC .............. *E04B 9/02* (2013.01); *A61B 90/35* (2016.02); *A61B 90/40* (2016.02); *A61G 13/108* (2013.01); *E04B 9/003* (2013.01); *A61B 2090/401* (2016.02); *E04B 2009/026* (2013.01)

(58) Field of Classification Search
CPC ...... E04B 9/02; E04B 9/003; E04B 2009/026; A61G 13/108; A61B 90/35; A61B 90/40; A61B 2090/401
See application file for complete search history.

(56) References Cited

U.S. PATENT DOCUMENTS

| | | | | |
|---|---|---|---|---|
| 1,918,008 A | * | 7/1933 | Worrell ................ | F24F 13/15 49/82.1 |
| 2,621,579 A | * | 12/1952 | Person ................ | F24F 13/062 251/279 |
| 2,845,855 A | * | 8/1958 | Burns ................ | F21S 8/02 362/260 |
| 2,884,512 A | * | 4/1959 | Wakefield ............ | F21V 33/0088 362/149 |
| 2,962,582 A | * | 11/1960 | Croft ................ | F21K 99/00 362/149 |
| 3,252,400 A | * | 5/1966 | Madl, Jr. ............ | F24F 3/161 454/187 |
| 3,320,404 A | * | 5/1967 | Roux ................ | F24D 5/02 165/53 |
| 3,774,522 A | * | 11/1973 | Marsh ................ | A61G 10/02 454/187 |
| 4,034,659 A | * | 7/1977 | Raider ................ | F24F 3/161 454/298 |
| 4,683,699 A | * | 8/1987 | Larsson ............... | E04B 9/02 52/506.08 |

(Continued)

*Primary Examiner* — Jeanette E Chapman
(74) *Attorney, Agent, or Firm* — Barta, Jones & Foley, P.C.

(57) ABSTRACT

An air frame system includes a frame body defining one or more openings and a plurality of air passages along an inner periphery of the one or more openings. The air frame system further includes a light assembly removably coupled to the frame body outside of the one or more openings.

17 Claims, 20 Drawing Sheets

(56) References Cited

U.S. PATENT DOCUMENTS

| | | | | |
|---|---|---|---|---|
| 5,136,486 | A * | 8/1992 | Burkarth | B60H 1/00371 |
| | | | | 362/149 |
| 5,313,375 | A * | 5/1994 | Jones | F21V 33/0088 |
| | | | | 362/149 |
| 5,620,369 | A * | 4/1997 | Spransy | F24F 3/161 |
| | | | | 454/187 |
| 6,220,576 | B1 * | 4/2001 | Chan | E01F 15/0438 |
| | | | | 256/13.1 |
| 6,351,920 | B1 * | 3/2002 | Hopkins | E04B 9/02 |
| | | | | 454/187 |
| 7,513,086 | B2 * | 4/2009 | Helmus | E04B 9/006 |
| | | | | 454/187 |
| 9,217,247 | B2 * | 12/2015 | Behling | E04L 39/32 |
| 2006/0130658 | A1 * | 6/2006 | Chang | B03C 3/09 |
| | | | | 96/77 |
| 2013/0344795 | A1 * | 12/2013 | Schreiber | F24F 13/078 |
| | | | | 454/293 |
| 2016/0273797 | A1 * | 9/2016 | Bruhnke | F24F 13/084 |
| 2017/0101779 | A1 * | 4/2017 | Schreiber | A61G 13/107 |

* cited by examiner

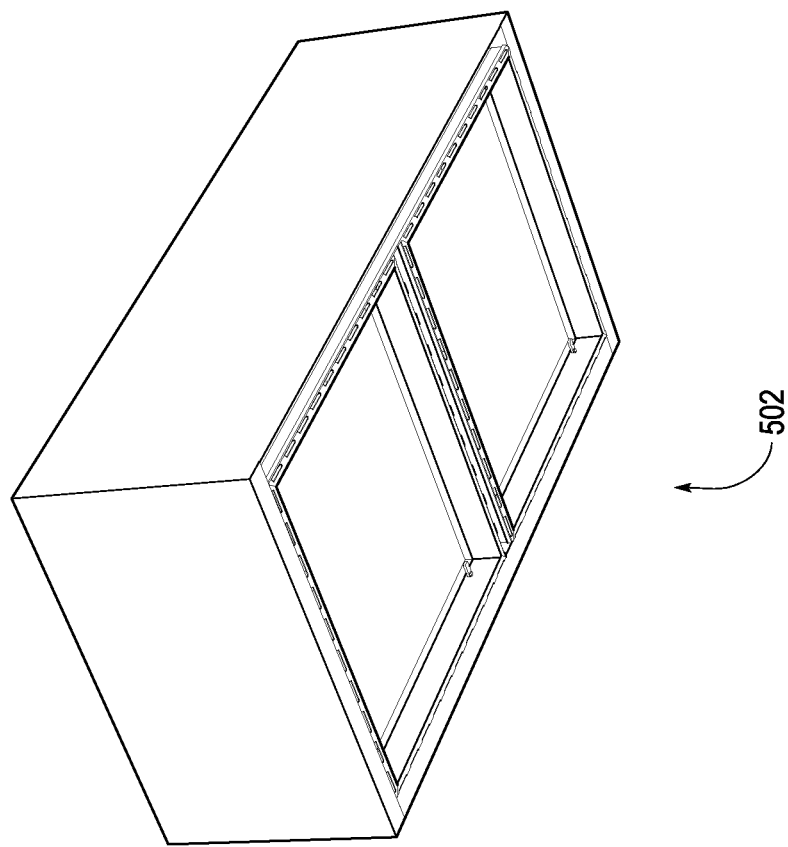
FIG. 22
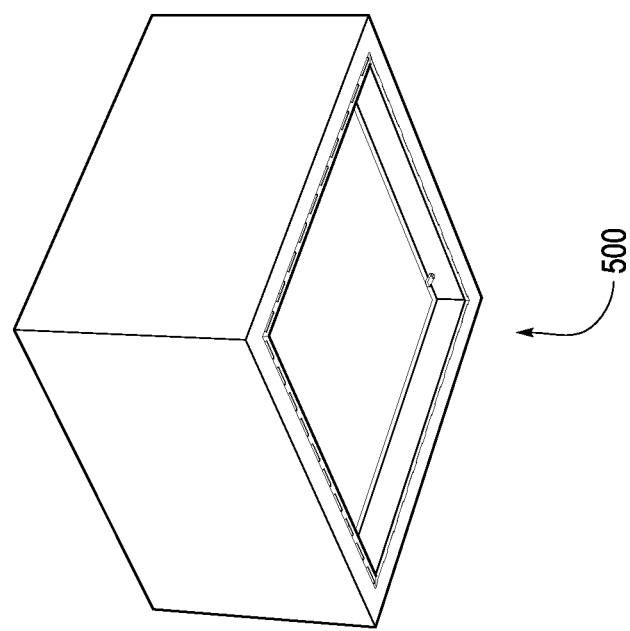

AIRFRAME SYSTEM AND METHOD OF CONTROLLING AIRFLOW

CROSS-REFERENCE TO RELATED APPLICATIONS

This nonprovisional application claims the benefit of and priority to U.S. Provisional Application No. 62/238,601, filed Oct. 7, 2015. The disclosure of the prior application is hereby incorporated by reference herein in its entirety.

BACKGROUND OF THE DISCLOSURE

Hospital operating rooms typically include surgical equipment and one or more lights that are located over a surgical site. The surgical equipment may be movable in relation to a surgical site target zone.

Additionally, air supply arrangement may be positioned within a ceiling directly above the surgical light and the surgical site target zone. The air supply arrangement may include vents through which filtered air is supplied and directed toward the surgical site. Sidewall vents return contaminated air from the perimeter of the room to an air filtration system positioned upstream of the supply air array. The air filtration system supplies filtered air to the room through the supply air array with unidirectional, downward airflow.

Because the surgical equipment (e.g., surgical light) may be positioned directly over the surgical target zone, the surgical equipment may block airflow generated by the air supply arrangement and create a low pressure zone underneath the surgical equipment. The low pressure zone causes air turbulence underneath the surgical equipment. Due to turbulent airflow, various contaminants generated through a surgical procedure may be circulated within the surgical environment. For example, surgical staff may carry particulate and bacterial contaminants that may be dispersed directly above a surgical site in the absence of filtered, downward, unidirectional flow. Further, bone fragments, biological fluids, and blood may be projected upward toward the surgical equipment, which is cleaned and sterilized between surgical procedures.

Accordingly, a need exists for a system and method of providing uninterrupted, reduced turbulence airflow within a sterile field and underneath surgical equipment. A need also exists for a system and method that reduces the possibility of contaminants being dispersed over and within a surgical site.

SUMMARY OF THE DISCLOSURE

Certain embodiments of the present disclosure provide an air frame system that includes a frame body defining one or more openings and a plurality of air passages along an inner periphery of the one or more openings. The air frame system further includes a light assembly removably coupled to the frame body outside of the one or more openings.

Certain embodiments of the present disclosure provide an operating room that may include a floor connected to walls, and a ceiling connected to the walls, wherein a surgical site is disposed at an area between the floor, the walls, the and ceiling. The operating room includes an airframe coupled to the ceiling and configured to provide captive airflow therein to create air pressure to direct air into a sterile field of the operating room. The operating room further includes an integrated light system removably coupled to the airframe without hardware.

Certain embodiments of the present disclosure provide an air frame system the includes plural air delivery mounting members, each having rivet alignment holes and airflow openings configured to direct airflow therethrough, the air delivery mounting members defining one or more air frames. The air frame system further includes a lighting module with a rivet track coupled to the rivet alignment holes of the air delivery mounting members such that the lighting module is between air delivery mounting members and one or more structural mounts coupled to an outside portion of one or more air delivery mounting members such that the one or more structural mounts are located along a perimeter of an airfield.

BRIEF DESCRIPTION OF THE DRAWINGS

FIG. 22 is a bottom perspective view of light, air-diffusers, according to an embodiment of the present disclosure.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide an airflow system that includes a frame structure that allows for proper airflow within the surgical target zone even when surgical equipment is positioned above the surgical target zone. For example, in various embodiments, low pressure zones that could cause air turbulence underneath the surgical equipment are reduced or eliminated. As such, in various embodiments, because the turbulent airflow is reduced or eliminated, various contaminants generated through a surgical procedure are not circulated within the surgical environment.

One or more embodiments provide an airframe structure that is configured to channel air, which may be filtered, sterilized or purified, to the surgical target zone with minimal or no air turbulence underneath the surgical equipment. Various embodiments provide an integrated and modular arrangement to effectively deliver airflow directly to the surgical target zone.

Figure 1:
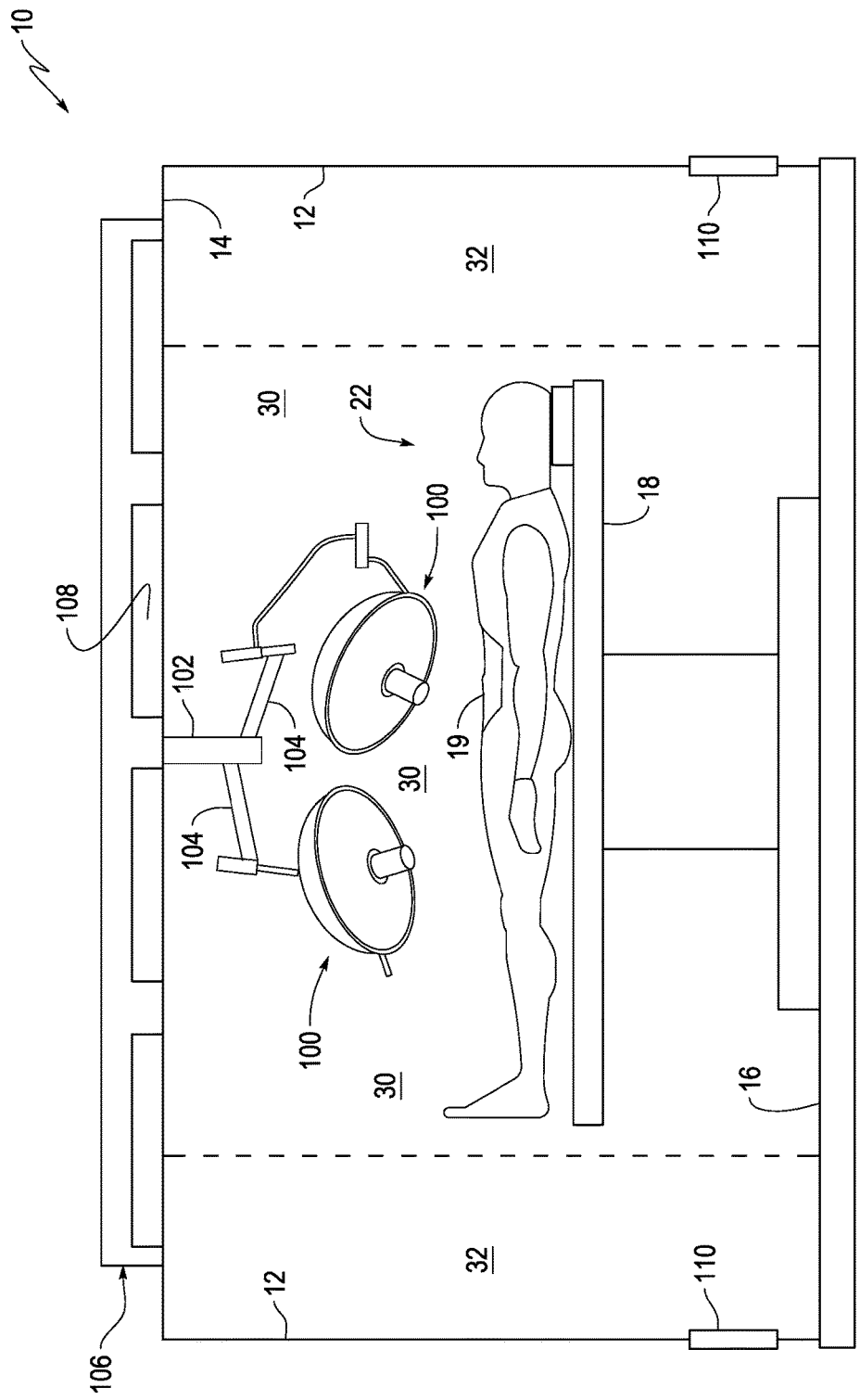
FIG. 1 illustrates a lateral view of an operating room, according to an embodiment of the present disclosure.

FIG. 1 illustrates a lateral view of an operating room 10, according to an embodiment of the present disclosure. The operating room 10 may be defined by walls 12, a ceiling 14, and a floor 16. An operating table 18 may be supported on the floor 16. The operating table 18 may include a support bed 20 that is configured to support a patient 22. A surgical site 19 may be located on the patient 22.

Surgical equipment, which in the illustrated embodiment is a surgical light system 100 is suspended from the ceiling 14 above the operating table 18, which may define a sterile field 30. A support beam 102 extends downwardly from the ceiling 14. One or more boom arms 104 may extend from the support beam 102. As shown in FIG. 1, two surgical light assemblies 100 may be coupled to two separate and distinct boom arms 104. Alternatively, more or less surgical light assemblies 100 than shown may be used. It should be appreciated that surgical light system 100 is shown only for illustrative purpose and different or additional surgical equipment may be suspended from the ceiling 14.

A supply air array 106 (also referred to as an air frame system) is secured to the ceiling 104. The supply air array 106 is configured to direct airflow into the operating room 10 and in various embodiments defines a supply air frame. The supply air array 106 may include one or more air diffusers 108 (or air delivery modules). Additionally, one or more return vents 110, which may be secured to one or more walls 12 are provided. In the illustrated embodiment, the supply air array 106 directs airflow into the operating room through the diffusers 108. The airflow passes into the return vents 110, which channel the airflow back into the supply air array 106, where the airflow is filtered and directed back into the operating room through the air diffusers 108. As discussed in more detail herein, the supply air array 106 is configured to control airflow in operating room 10 such that air is directed from the sterile field 30 to a non-sterile field 32 without being recirculated back into the sterile field 30. Thus, airflow is directed from the supply air array 106 into the sterile field 30 then to the non-sterile field 32 and finally into the one or more return vents 110.

The supply air array 106 is also configured to include an integrated lighting structure that includes a plurality of light sources as described in more detail herein. Accordingly, in various embodiments the supply air array 106 defines an integrated unit that may be installed with electrical components and air supplies connected to a single structural element. Thus, a laminar airflow is created directly to the surgical target zone that creates an airflow pressure to reduce or prevent turbulence, which is also being lit by the integrated lighting.

Figure 2:
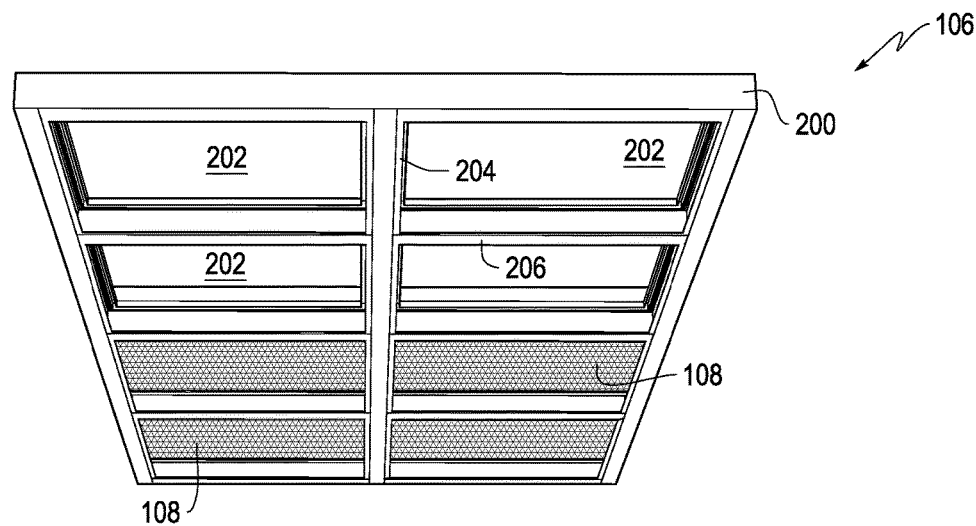
FIGS. 2 and 3 illustrate perspective bottom views of a supply air array, according embodiments of the present disclosure.

FIG. 2 illustrates a perspective bottom view of the supply air array 106, according to an embodiment of the present disclosure. The supply air array 106 in the illustrated embodiment includes a lower frame 200 having a plurality of openings 202 defined therein by cross-members 204 and 206. It should be noted that although the illustrated embodiment shows a 2 cell×4 cell array, the supply air array 106 may be sized differently, including having a single opening 202. Additionally, the openings 202 may be sized and shaped differently than illustrated, for example, based on design requirements or constraints. In the embodiment shown in FIG. 2, the front four openings 202 are illustrated with nothing therein and the back four opening 202 illustrate air diffusers 108 coupled within the openings 202. As can be seen, the air diffusers 108 are coupled with the openings 202 such that the air diffusers 108 are recessed within the openings 202 in this embodiment.

Figure 3:
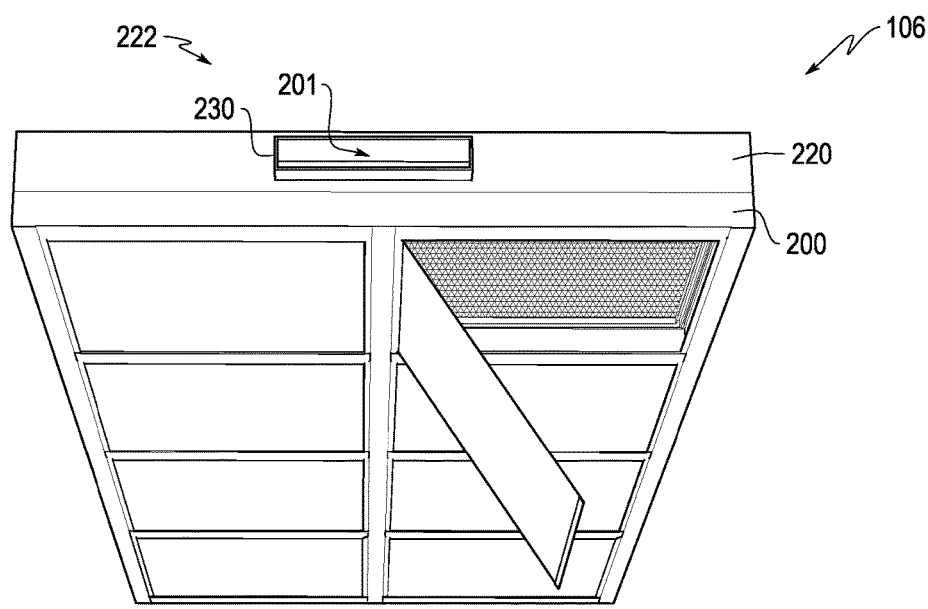
Figure 4:
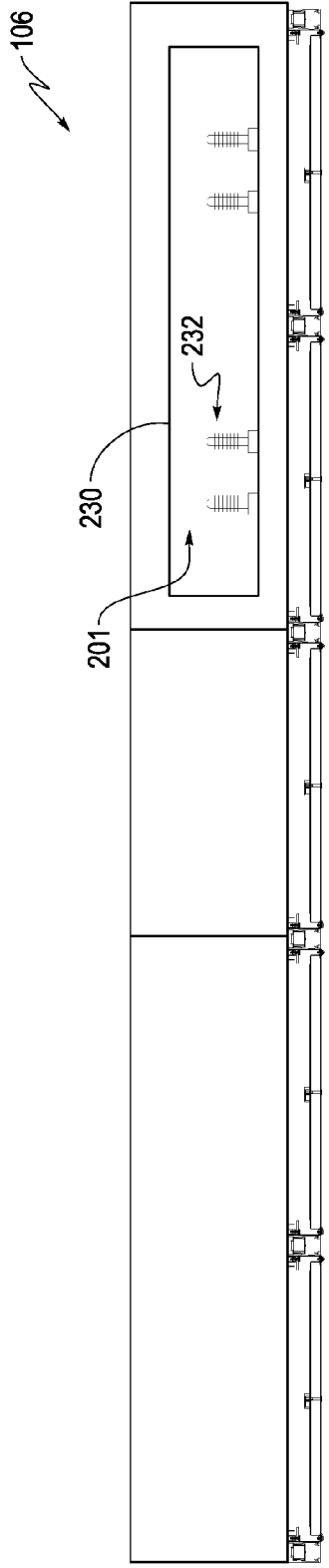
FIGS. 4 and 5 illustrate lateral internal views of a supply air array, according to an embodiment of the present disclosure.

FIG. 3 illustrates a perspective bottom view of the supply air array 106 in which all of the openings have air diffusers 108 coupled therein and shows that the air diffusers 108 may be hingedly mounted to one side of the openings 202 such that access may be provided within the openings 202, as well as to both sides of the air diffusers 108 (e.g., to clean the air diffusers 108 or to install HEPA filters). As can be seen in FIG. 4, a top cover 220 is coupled above the lower frame 200 (e.g., by an airtight seal) to define a pressure air space above the lower frame 200. In the illustrated embodiment, an air coupler 222 is provided on one end of the top cover 220 to allow coupling to an air supply that provides airflow into the top cover 220. The air coupler is made up of a supply air passage 201 and a supply air connection flange 230. There may be more than one air coupler 222 which may be positioned at any location on the top, the sides or the ends of the top cover 220. In operation, air supplied into the top cover 220 is directed into the sterile field 30 (shown in FIG. 1) to define a non-turbulent laminar flow.

Figure 5:
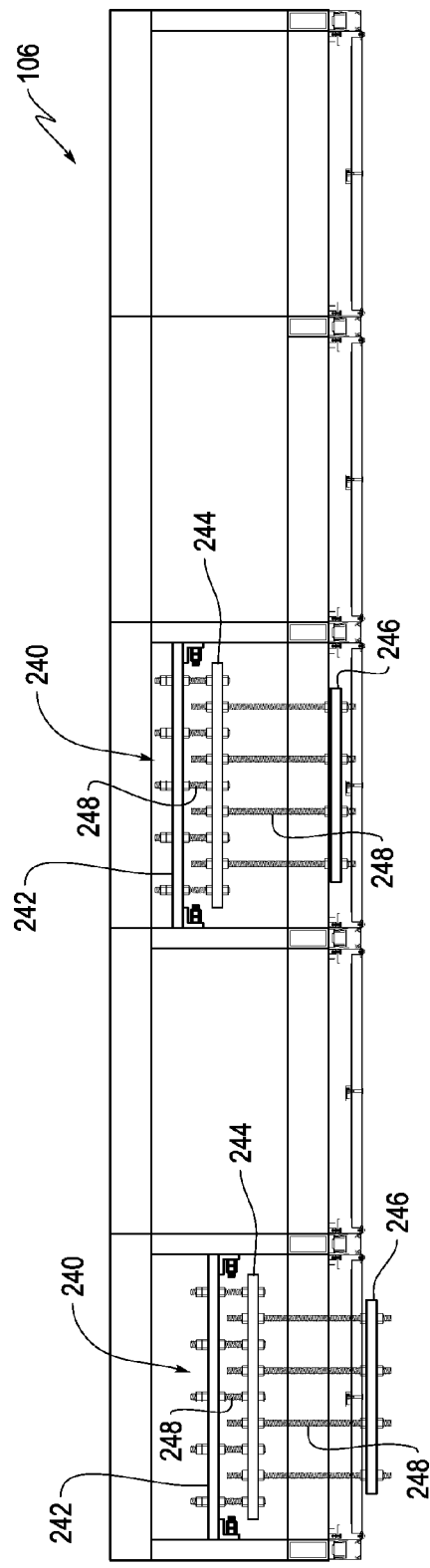
Figure 6:
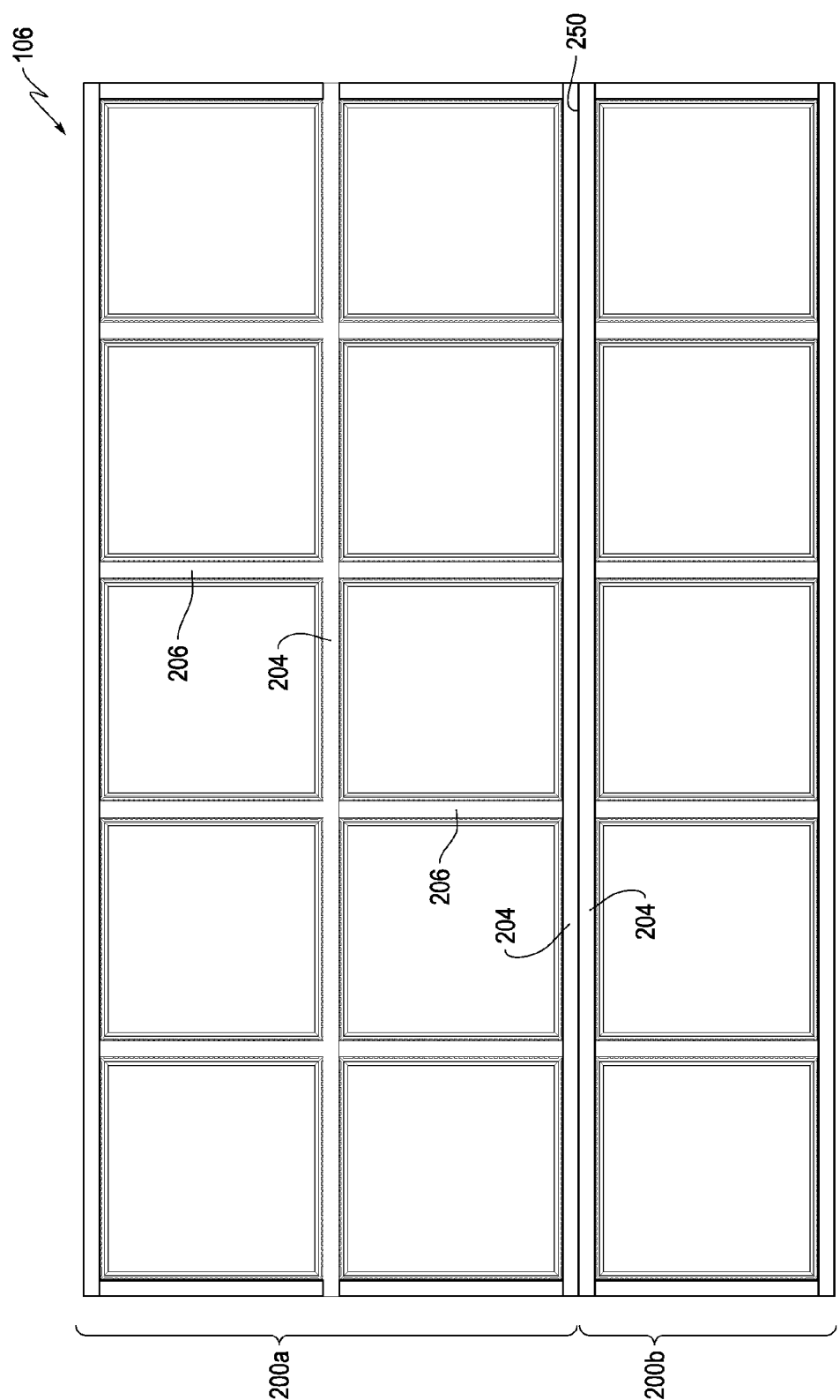
FIG. 6 illustrates a bottom plan view of a supply air array, according to an embodiment of the present disclosure.

FIGS. 4 and 5 are elevation views of the supply air array 106 and FIG. 6 is a bottom plan view of the supply air array 106. In the illustrated embodiment, an air supply connection 230 may be provided that includes a cleansing system, shown as a sterilization system 232. As discussed herein, the cleansing system may include an air filtering system, the sterilization system 232 and/or an air purifying system. The cleansing system may be placed at any location within the supply air array 106 or upstream of the supply air array 106.

The cleansing system is positioned up stream of the opening 202 such that air that passes through the opening 202 is cleansed.

The supply air array 106 includes an adjustable mounting arrangement 240 that allows for varying the height of components, such as the boom arm 102 mounted within the openings. In particular, the adjustable mounting arrangement 240 defines mounting locations within the each opening 202 of the lower frame 200. The adjustable mounting arrangement 240 in the illustrated embodiment includes a mounting plate 242 that may be mounted within the opening 202 at different locations, in particular, different vertical locations within the opening 202. For example, predefined mounting locations (e.g., mounting bores) may be located on opposing walls of the opening 202 for coupling thereto of the mounting plate 242 (e.g., bolt mounting of the mounting plate 242 to walls of the opening 202). The predefined mounting locations provide a coarse mounting arrangement within the opening 202. For example, as can be seen in FIG. 5, the two mounting plates 242 are mounted at different vertical heights within respective openings 202.

The mounting plates 242 couple to a secondary plate 244 that allows for adjustable mounting thereto of a bottom plate 246. For example, plural bolts 248 may couple the secondary plate 244 (or intermediate plate) to the bottom plate 244 to allow finer height adjustment within the opening 202. As can be seen in FIG. 5, the bottom plate 244 in the different openings 202 extend a different distance from the secondary plate 244 such that the bottom plate 244 in each of the openings 202 is positioned at different vertical heights. As should be appreciated, components to be mounted within each of the openings 202 may be mounted at the same or different vertical heights.

As shown in FIG. 6, the cross-members 204 and 206 define an airtight arrangement wherein airflow is directed around the cross-members 204 and 206 into the openings 202, which will be described in more detail herein. Additionally, separate lower frames 200 may be coupled together at a seam 250. For example, in the illustrated embodiment, a lower frame 200a defining a 2 cell×5 cell supply air array 106 is coupled with a lower frame 200b defining a 1 cell×5 cell supply air array 106. The lower frames 200a and 200b may be coupled together using any suitable fastening arrangement, such as coupling together by bolts.

Figure 7:
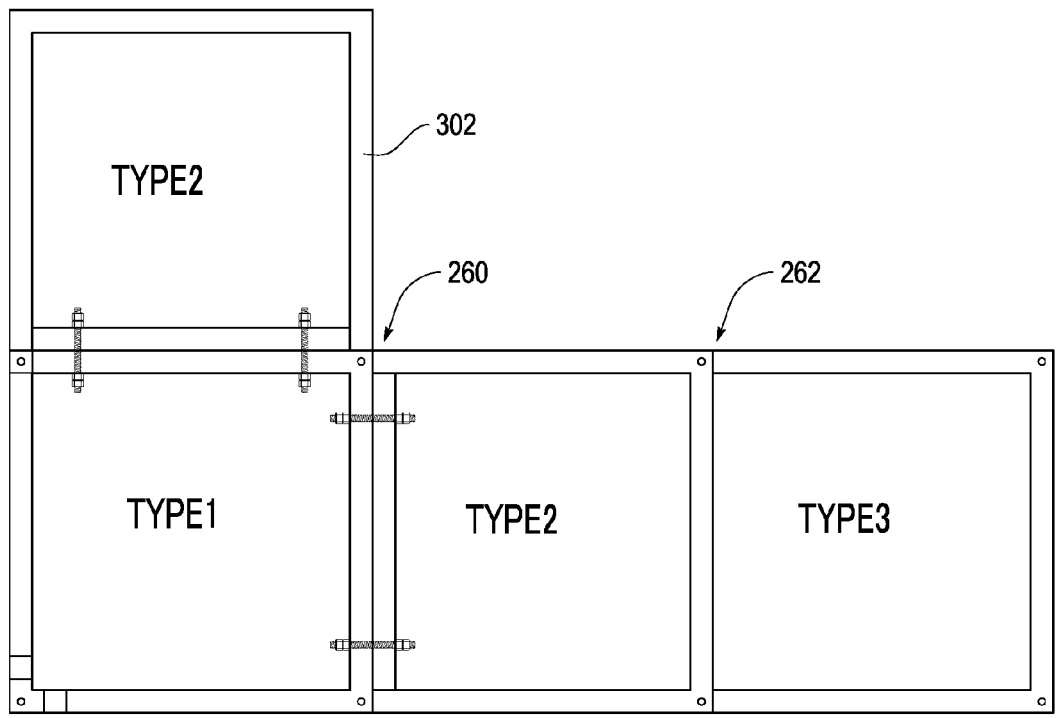
FIG. 7 illustrates a bottom plan view of modular units coupled together, according to an embodiment of the present disclosure.
Figure 8:
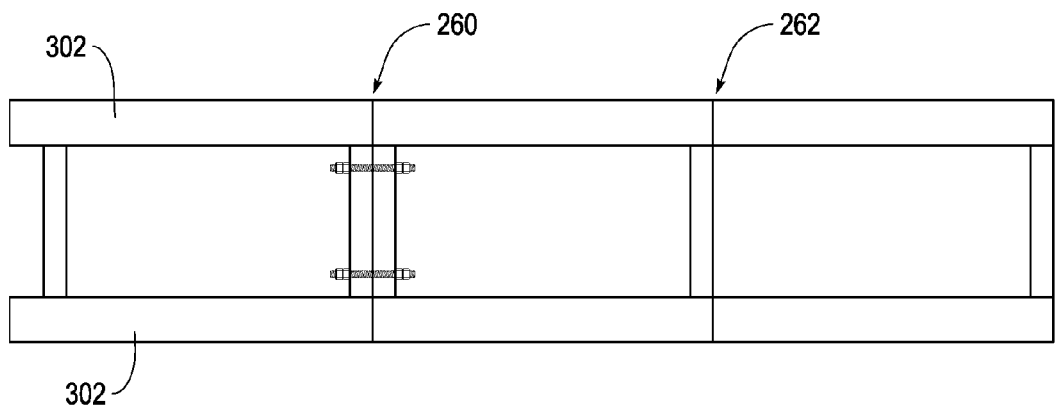
FIG. 8 illustrates a side elevation view of modular units coupled together, according to an embodiment of the present disclosure.

As illustrated in FIGS. 7 and 8, different modular elements (shown as three different types of modular units) defining the openings 202 in the supply air array 106 may be coupled together with a bolted connection 260 or a welded connection 262. Thus, different sized and shaped supply air arrays 106 may be provided that include different types of modular elements. The different types of modular elements may include different elements, such as the diffusers 108, lights or other components that would be desirable or needed in the operating room 10. In some embodiments, the supply air array 106 may include the lower frame 200 with components, a light housing with components, a wireway with components and/or a hinged screen and airflow control damper (such as the airflow dampers 108). In various embodiments, plural air diffusers 108 are installed with the top cover 220 having a top or side mounted air duct collar.

Figure 9:
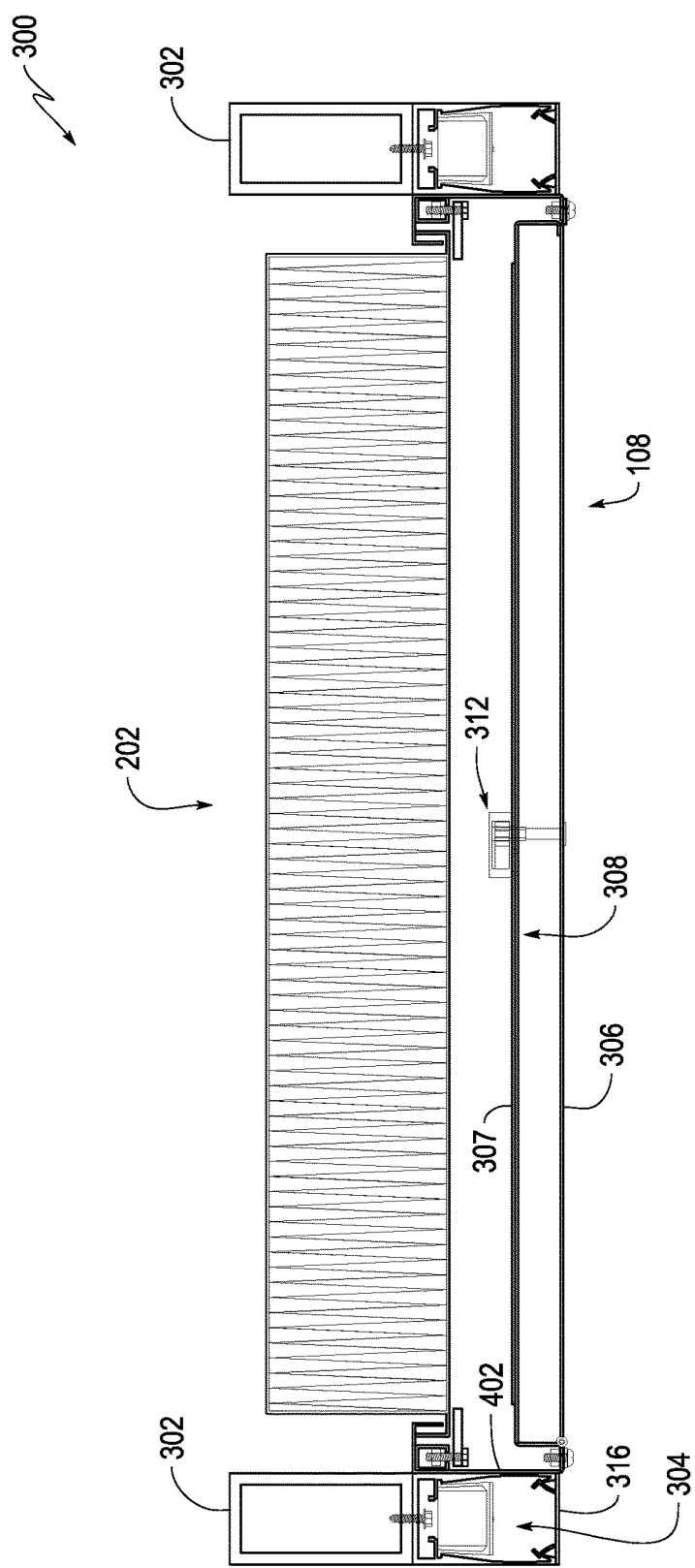
FIGS. 9 and 10 illustrate side elevation views of a portion of a supply air array showing a diffuser screen, damper and filter arrangement, according to an embodiment of the present disclosure.

FIG. 9 illustrates a single modular element 300, according to an embodiment of the disclosure. The modular element 300 is defined by the opening 202 between supporting members, which in this embodiment are hollow structural section (HSS) tube frames 302 that may be mounted, for example, to a truss system, such as described in co-pending patent application Ser. No. 15/288,168 entitled Equipment Support System and Method of Supporting Equipment in a Surgical Environment, filed on Oct. 7, 2016, or to the ceiling 14. The HSS tube frames 302 may include a snap-fit light assembly 304 coupled to the HSS tube frames 302 (illustrated as coupled with a bolt). The light assembly 304 may be a suitable light source for an operating room environment and include a light lens 316 at a bottom surface thereof.

Figure 17:
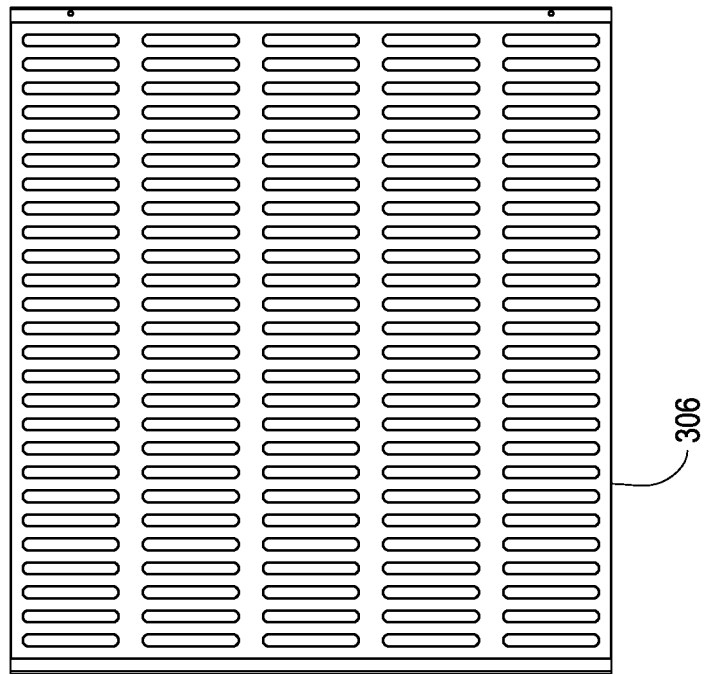
FIG. 17 is a bottom plan view of a guillotine damper, according to an embodiment of the present disclosure.
Figure 17:
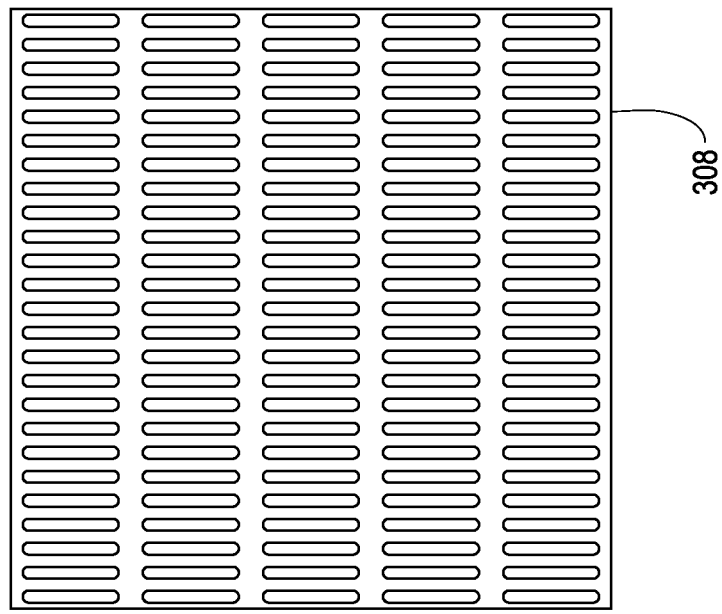

In the embodiment of FIG. 9, the air diffuser 108 includes a screen 306 and a damper 308 (also shown in FIG. 17) that extend across the opening 202, which may be adjusted (e.g., rotated) by a tool, such as an Allen wrench, causing the damper 308 to open or close (in a guillotine type configuration). The screen 306 and damper 308 are coupled together as a single unit and hingedly coupled to one end of the opening 202, for example, to a lower end of an airframe channel 402 in which the light assembly 304 is coupled. The damper top plate 307 and damper 308 arrangement includes a damper adjustment mechanism 312 that allows for movement of the damper top plate 307 and damper 308 relative to each other to adjust airflow therethrough. Thus, an airflow control damper may be defined.

Figure 10:
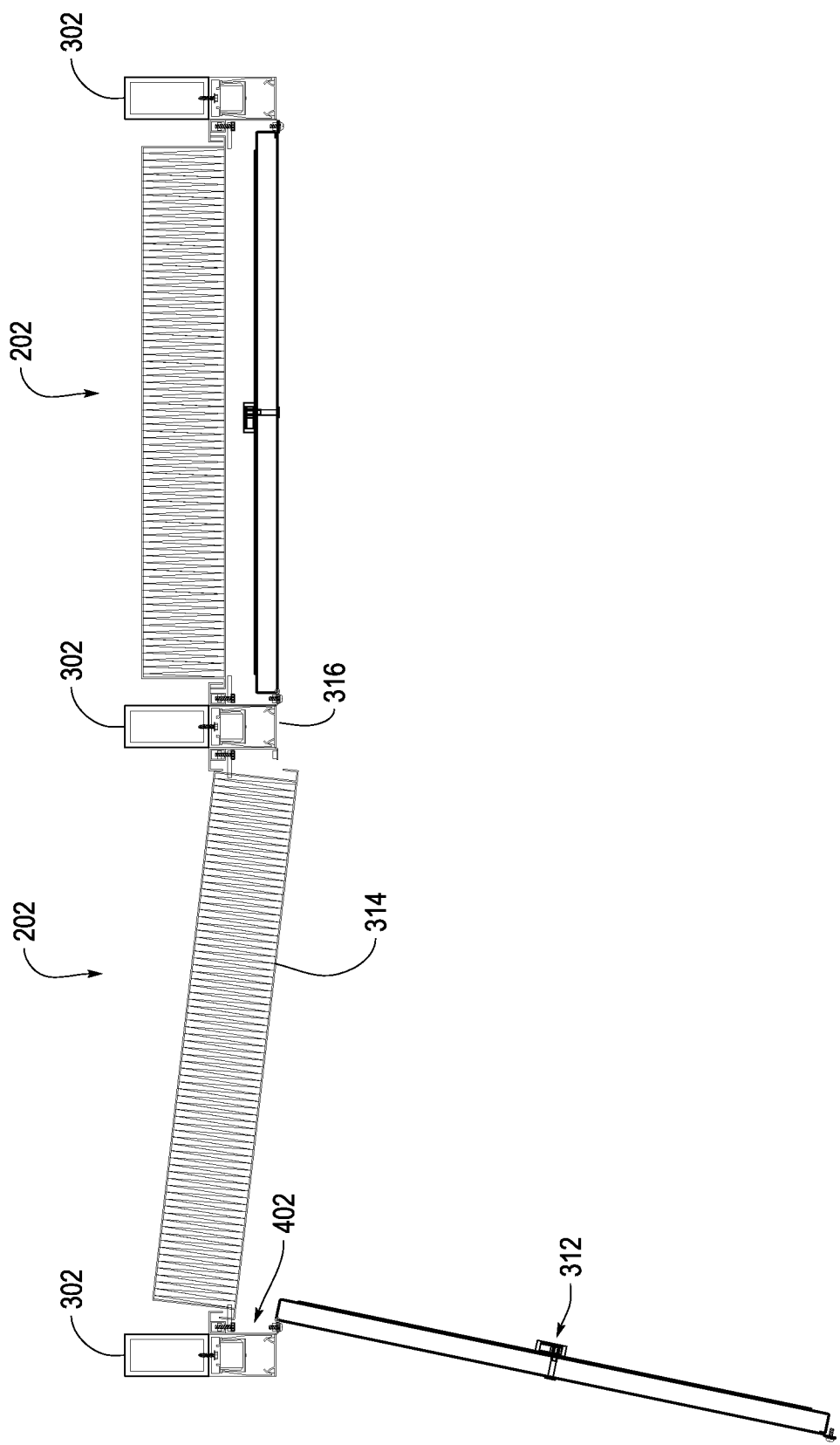
Figure 12:
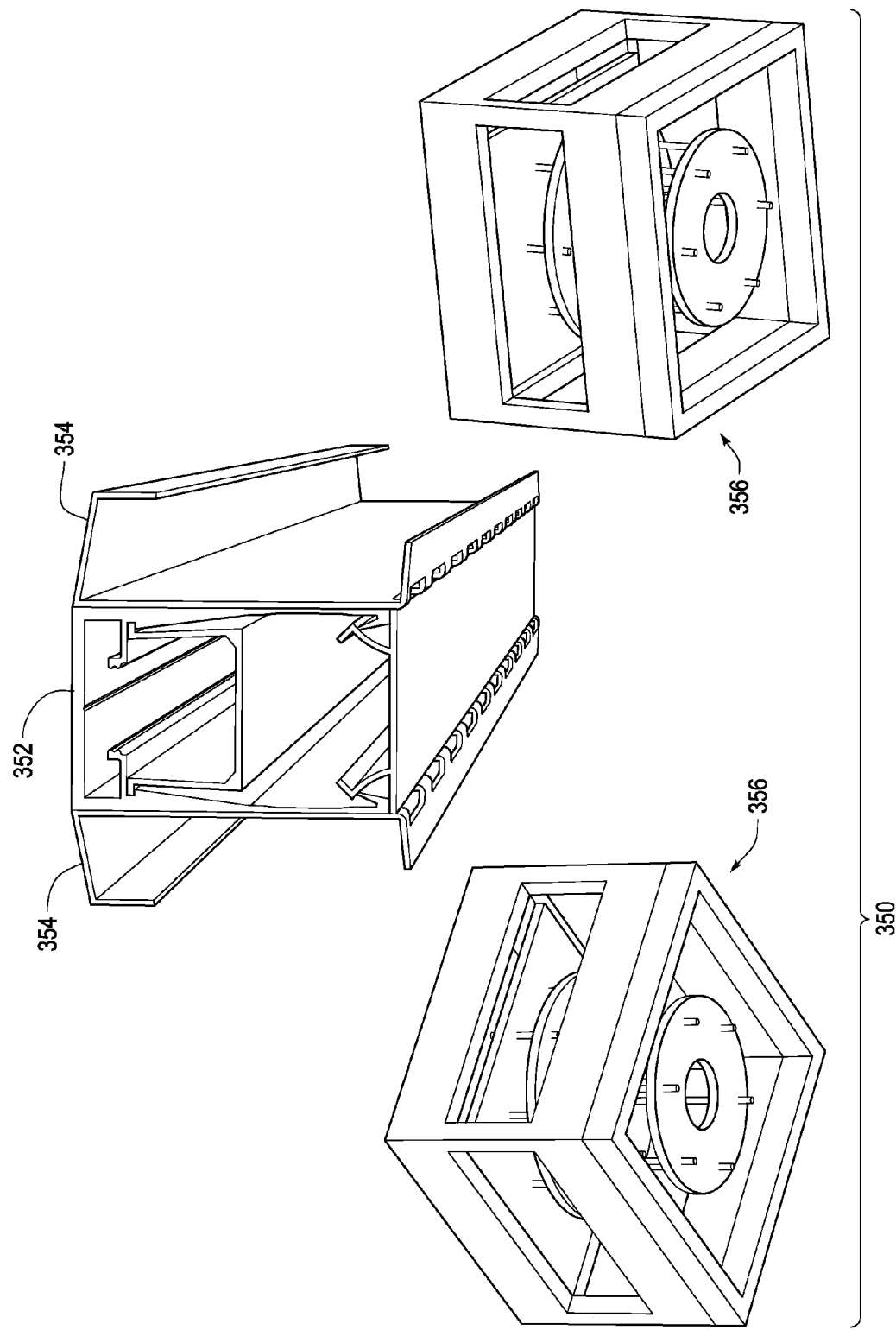
FIG. 12 illustrates an assembly and structural mounts, according to an embodiment of the present disclosure.

As can be seen in FIG. 10, an air cleansing member, illustrated as an air filter 314, such as a high-efficiency particulate arrestance (HEPA) filter may be provided. The air filter 314 is removably coupled within the opening 202 to allow for removal and replacement within the opening 202. For example, a knife edge seal and HEPA lock may be provided as illustrated in FIG. 12.

Figure 11:
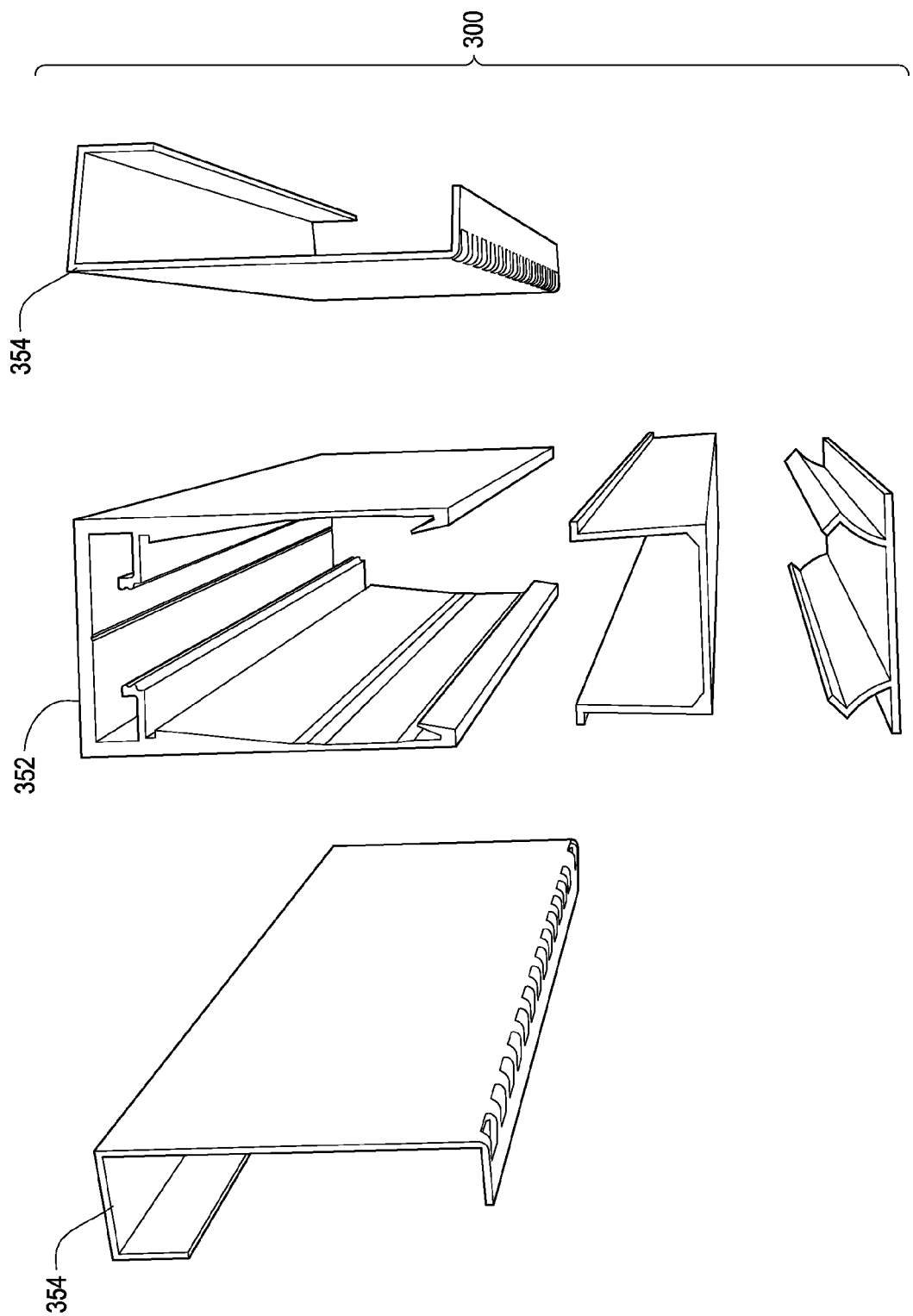
FIG. 11 illustrates a perspective view of components, according to an embodiment of the present disclosure.

Various embodiments, thus, provide air delivery and lighting in a modular, easily to install configuration. In various embodiments, an airframe system 350 may be provided, components of which are shown in FIG. 11. The components may be coupled together in different configurations as desired or needed, and as discussed herein. FIG. 11 illustrates base components in accordance with some embodiments. Illustrated in FIG. 11 are portions of various components, the components include a portion of a lighting module 352 (shown in an exploded view, the elements of which couple together without fasteners) and portions of air delivery modules 352, which may be sized and shaped based on a particular configuration. In various embodiments, the modules define separate systems or sub-systems to deliver the different features, including lighting and air. As illustrated in FIG. 12, the lighting module 352 is coupled to air delivery modules 352 (to define a lighting and air delivery sub-system) that is integrated with one or more structural mounts 356, such as by mounting these components together in a desired arrangement or configuration. It should be noted that in various embodiments, there is no penetration into the light cavity (e.g., inside the lighting module 352) as a result of the rivet holes for mounting being located in the airframe.

With reference now to FIGS. 13-16, various elements of the structural support for the supply air array 106 will now be described. In particular, the HSS tube frame 302 may be coupled with a light housing 400 (which may be embodied as the lighting module 352) having upper engagement members 402 and lower engagement member 409 that provide a snap fit coupling with the light assembly 304 and the lens 316, respectively (without the need for hardware fasteners). Additionally, the light housing 400 may be coupled with airframe support members 402 (which may be embodied as the air delivery modules 354) that are mounted to a support structure, such as the wall 12 or ceiling 14 of the operating room 10. The light housing 400 with the airframe support members 402 together define air frame channels of the supply air array 106. Variations and modifications are contemplated. For example, in some embodiments, a thumb tab release is provided in combination with a retainer clip 305 within the light housing 400 for easier removal of the components within the light housing 400.

Figure 13:
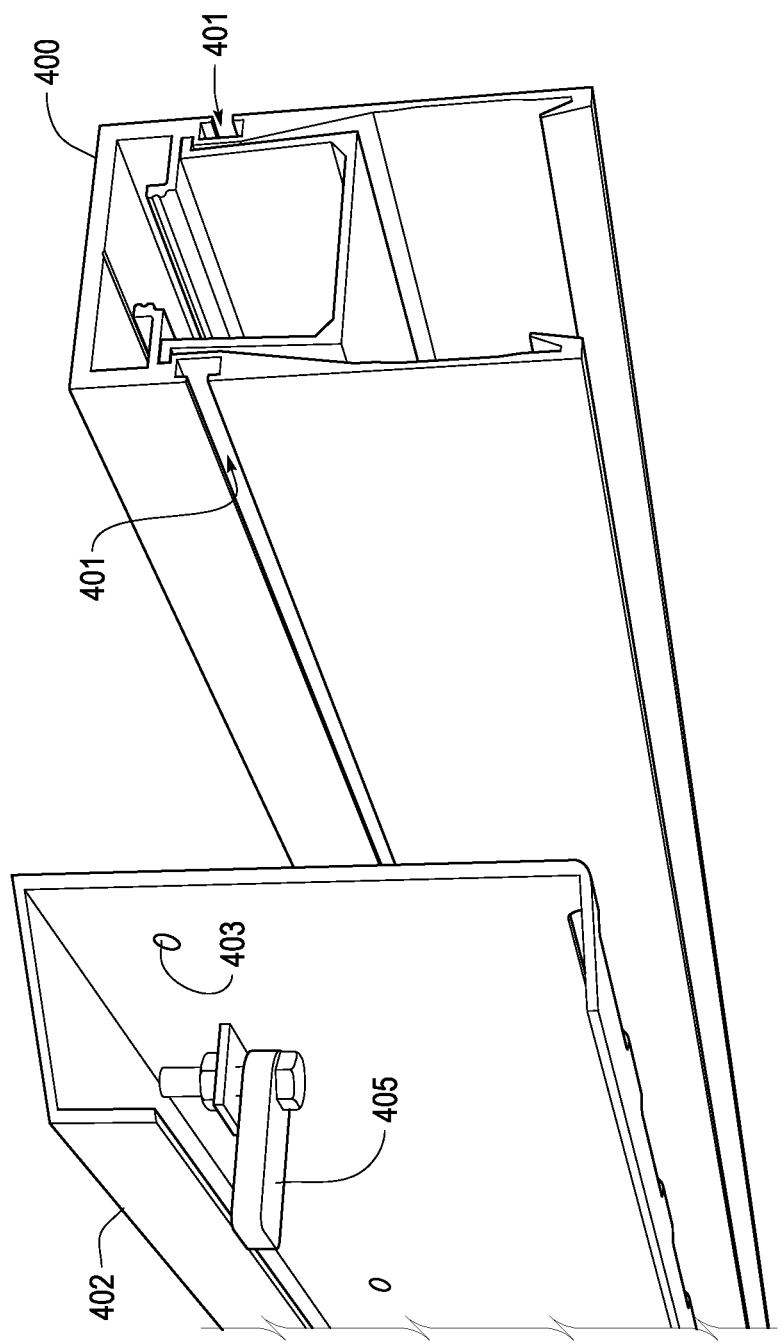
FIG. 13 illustrates a coupling arrangement, according to an embodiment of the present disclosure.
Figure 14:
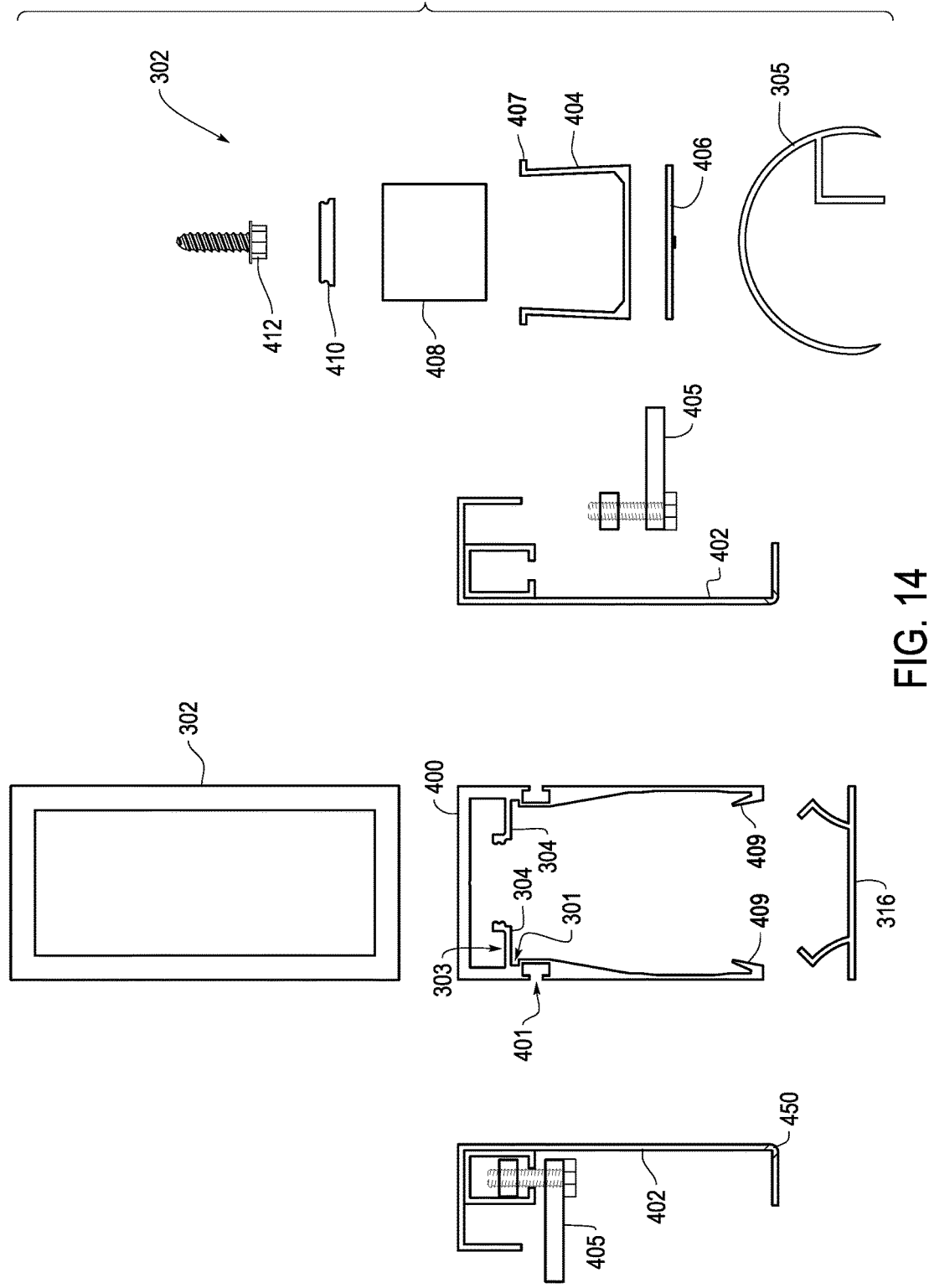
FIG. 14 is an exploded view of a light and air frame arrangement, according to an embodiment of the present disclosure.
Figure 15:
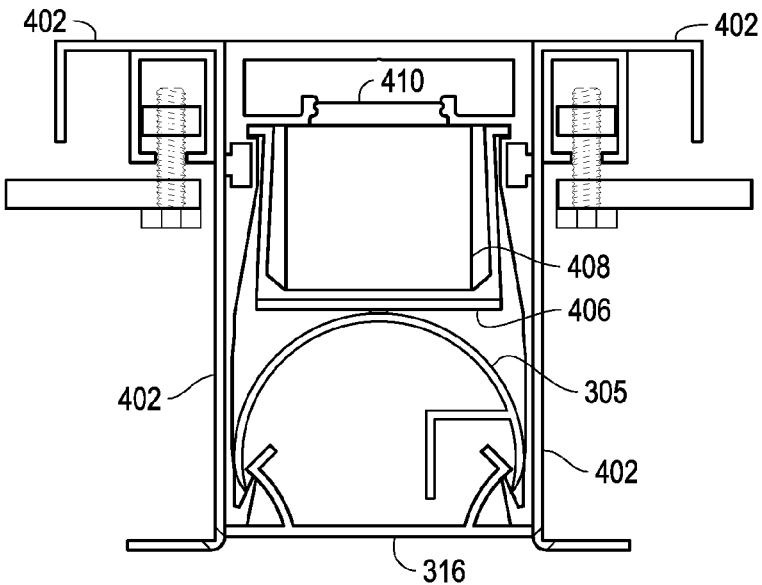
FIGS. 15 and 16 are side elevation views of assembled light and air frame assemblies, according to an embodiment of the present disclosure.
Figure 16:
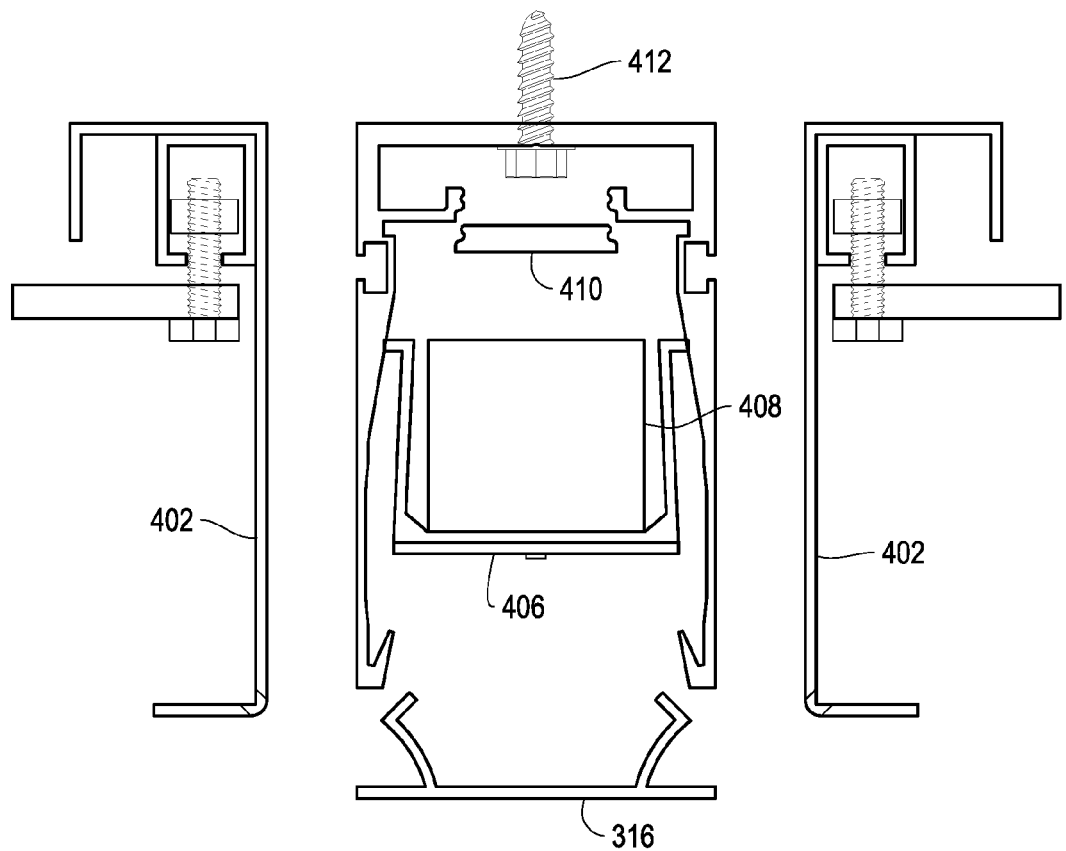

For example, as shown in FIG. 13, the light housing 400, which is illustrated as a light bar, includes mounting tracks, illustrated as rivet tracks 401 (illustrated as grooves extending longitudinally along the outer walls of the light housing 400) to which the airframe 402 is coupled by a rivet 403. As should be appreciated, the rivet tracks 401 allow the airframe 402 at any suitable location along the light housing 400. A HEPA lock 405 may be provided on the airframe 402 (illustrated as a locking arm coupled within the airframe 402) that allows for releasably securing a HEPA filter (or other filtering device) within the airframe 402 as discussed in more detail herein.

With respect to the light assembly 304 that is coupled within the light housing 400, a control housing 404 is coupled to an LED board 406 (light source) and is configured to receive therein a light controller 408. A wireway plug 410 is coupled to the bottom of a wireway cavity 303. A bolt 412 couples the light housing 400 to the HSS tube frame 302. The control housing 404 is configured with male protrusions 407 for snap fit engagement with an upper female cavity 301. In particular, the width of the light housing 400 narrows from bottom to top (as viewed in the Figures) such that control housing 404 is compressed and snap fit therein engaging the male protrusions 407 into the female cavity 301.

Figure 18:
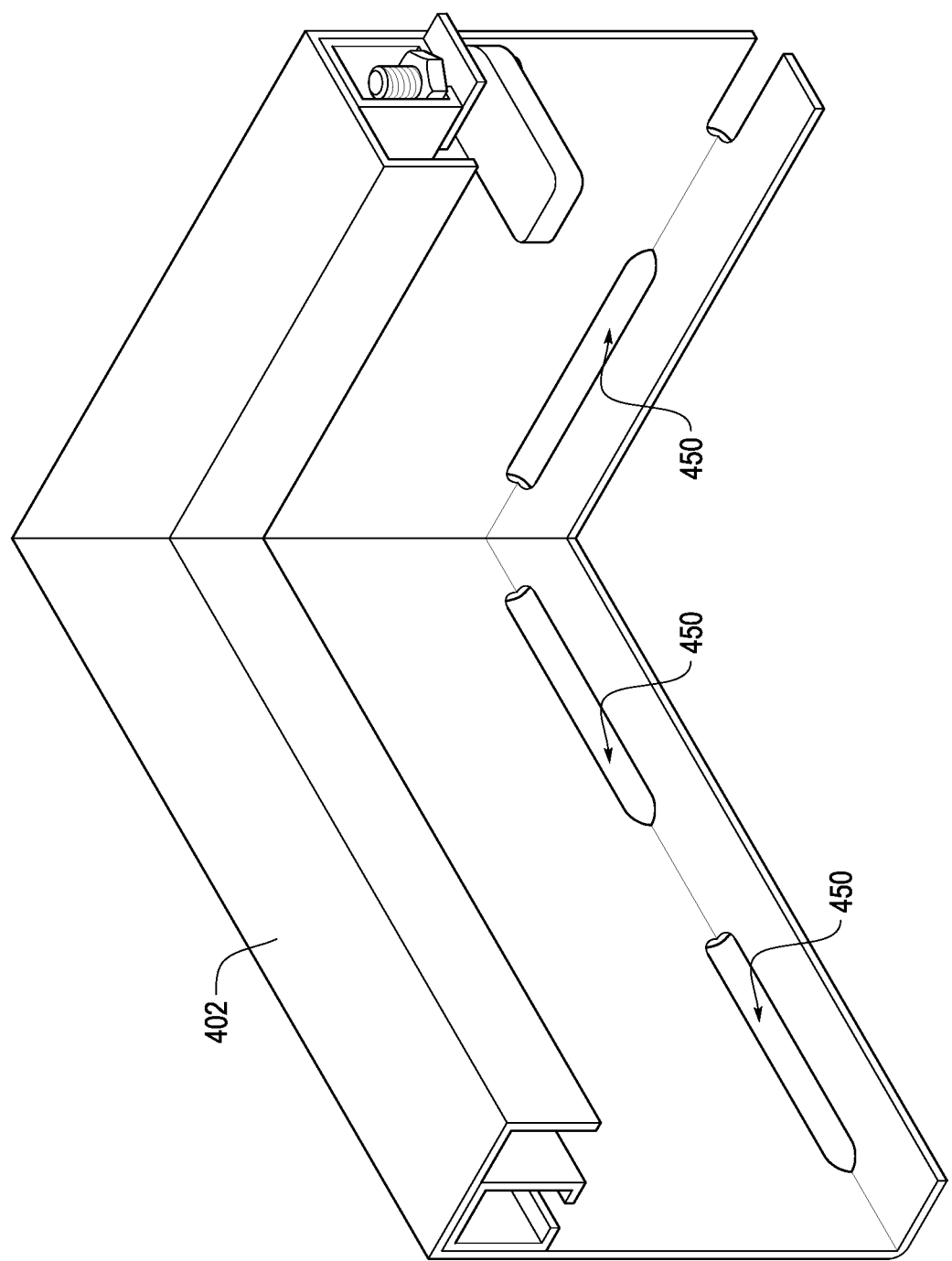
FIG. 18 is a top perspective view of an air channel frame showing air passages, according to an embodiment of the present disclosure.
Figure 20:
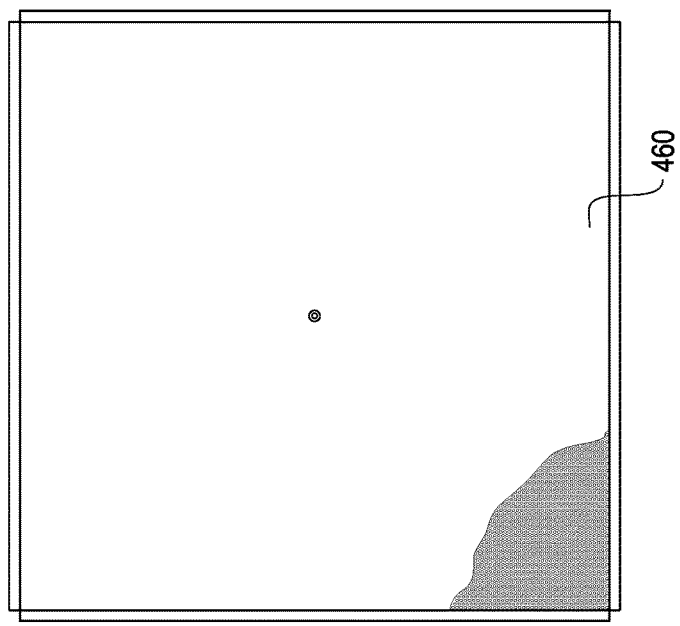
FIG. 20 is a bottom plan view of a diffuser screen, according to an embodiment of the present disclosure.
Figure 19:
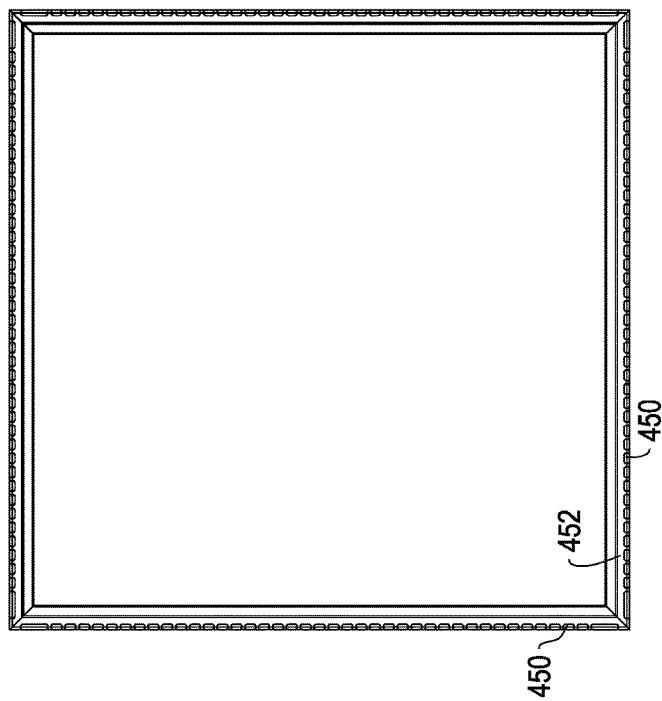
FIG. 19 is a bottom plan view of an air channel frame showing air passages, according to an embodiment of the present disclosure.
Figure 21:
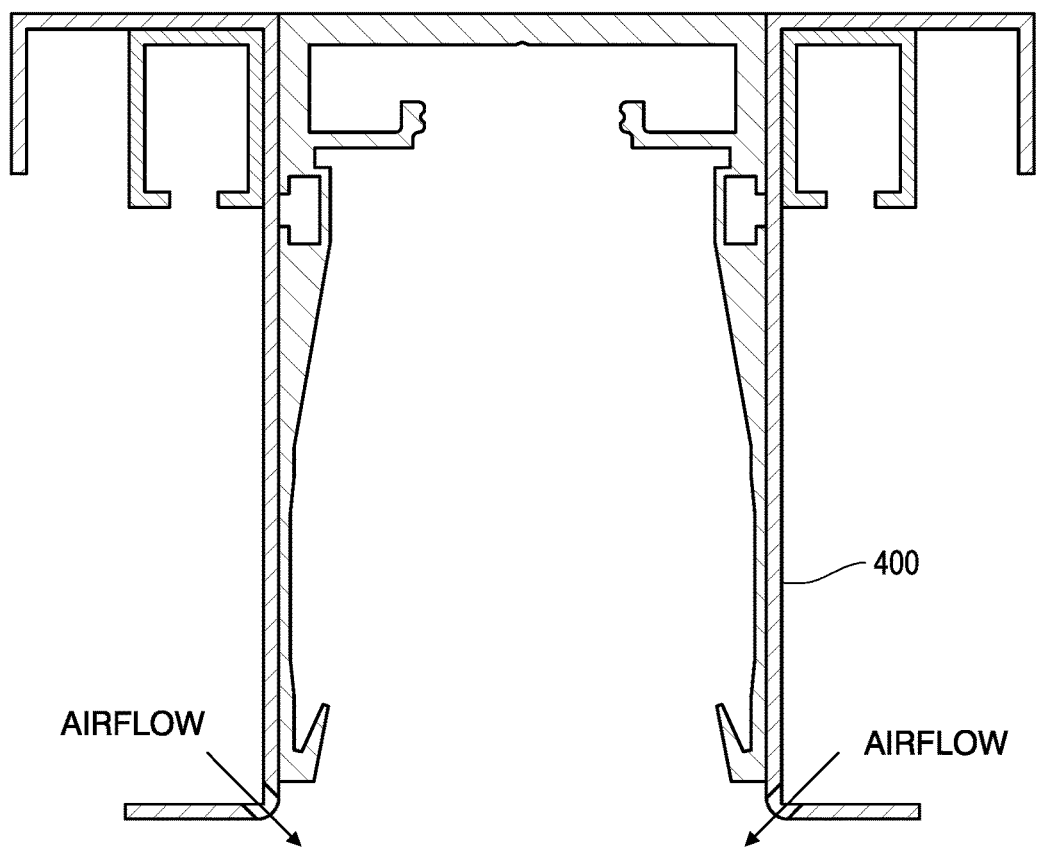
FIG. 21 is a side elevation view of a light assembly and air channel frame showing airflow, according to an embodiment of the present disclosure.

With reference now to FIGS. 18 and 19, the supply air array 106 includes the lower frame 200 that defines an air frame 402 with plural air passages 450 (airflow openings) along an inner edge 452 of each of the openings 202. For example, plural spaced apart openings 450 formed around the periphery of the opening 202 define airflow outlets. The plural air passages 450 allow airflow therethough, which is directed at an angle downward, for example, by the size, shape and orientation of the air passages 450. Thus, the air passages 450 are configured to direct airflow at an angle downward underneath the light housing 400. For example, an airflow outlet through the plural air passages 450 may be formed within the airframe directly adjacent to the periphery of a diffuser screen 460 as shown in FIG. 20 to direct airflow as shown by the arrows AF in FIG. 21. The airflow directed through the air passages 450 creates a pressure zone underneath the light housing 400 allowing for consistent pressure and airflow beneath the entire supply air array 106.

In some embodiments, a light diffuser structure may be formed in accordance with disclosure herein. For example, FIG. 22 illustrates a 2×2 light diffuser 500 and a 2×4 light diffuser 502. However, as should be appreciated, different sized configurations of light diffuser may be provided.

Figure 23:
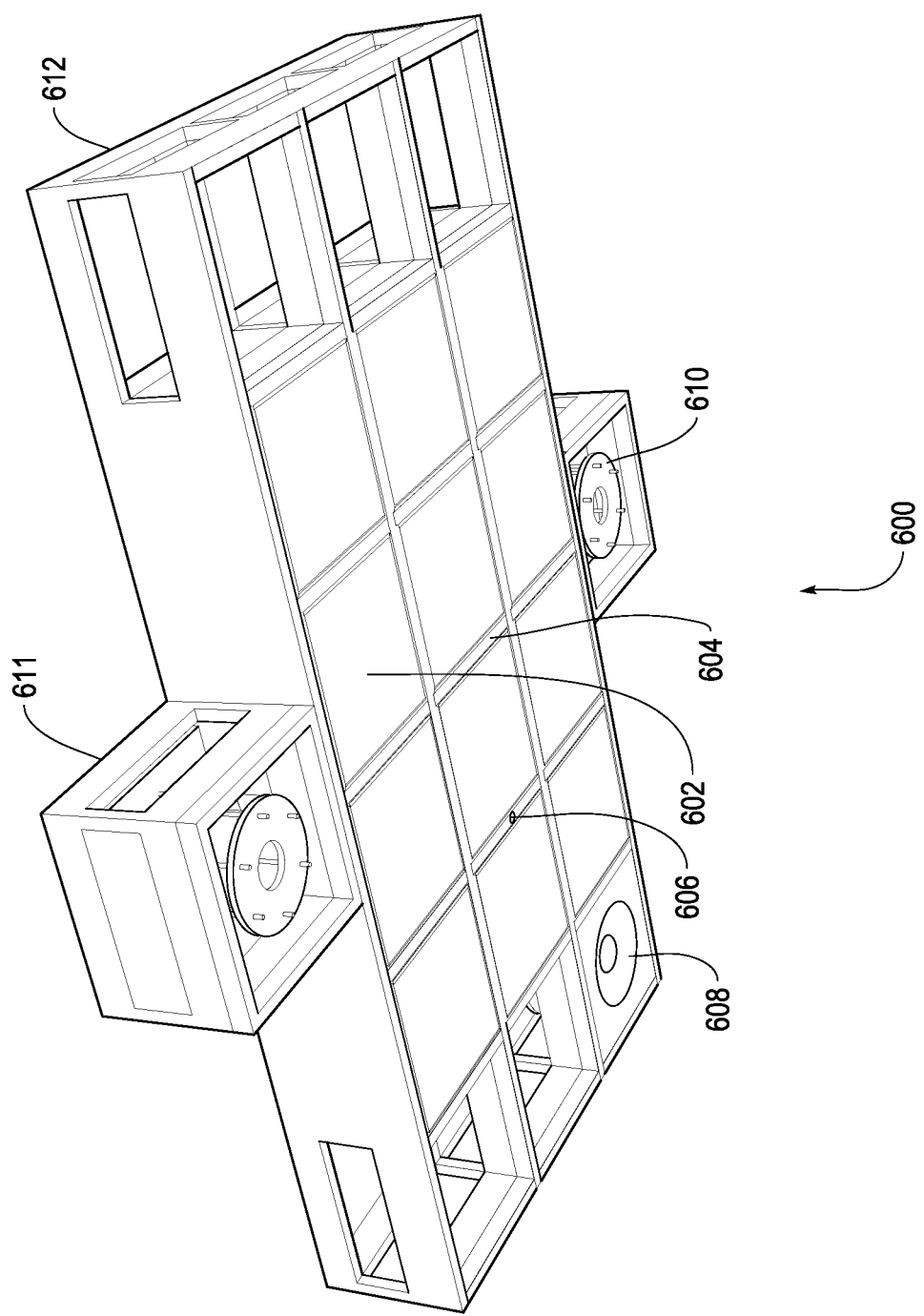
FIG. 23 is a perspective view of an integrated system with modules, according to an embodiment of the present disclosure.

Thus, various embodiments provide an air frame structure that can include lighting, wherein an air conduit is provided within the air frame structure to direct air into the sterile field 30. The various embodiments allow for the integration of multiple components into an easy to install and customizable system 600, such as shown in FIG. 23. The components may be formed or defined by modules or sub-systems that are coupled together as described herein. In the illustrated embodiment, the system 600 can include one or more air delivery modules 602, one or more lighting modules 604 (illustrated as LED lighting modules), one or more fire suppression modules 606, one or more audio/video modules 608 and one or more structural mounts 610, as described in more detail herein. Structural mounts may be configured as a single cell, Flex mount 610 or as a multiple cell arrangement 612. In the various embodiments, with a pressurized module (which may be embodied as or form part of the top cover 220 (shown in FIG. 3) that allows for simple and easy air source hook-up (e.g., contractor hook up, such as a single or dual S/A connection) and having improved quality and performance. The system 600, thus, provides single point air source connection instead of multiple connection points, resulting in less potential for air loss, less sealing and lower complexity. The system 600 also provides high performance controlled airflow, which includes controlling contaminants (that can be beneficial, such as to protect a patient in an operating room having the system 600 installed), using the plurality of modules as described herein.

It should be noted that in the system 600, the structural mounts 610 may be located (e.g., mounted) along the perimeter of the system 600, thereby being located along the perimeter of the airfield. In this configuration, air flow within the airfield is improved by not having the mounts within the portion of the system 600 that includes the airfield. It should also be noted that field connections can be made prior to equipment installation, thereby providing improved access for services, such as for power, data, audio/video, lighting and communications, among others. In some embodiments, one or more of the modules may include interface of connectors, such as a MedGas manifold with field piping performed prior to equipment installation.

Figure 24:
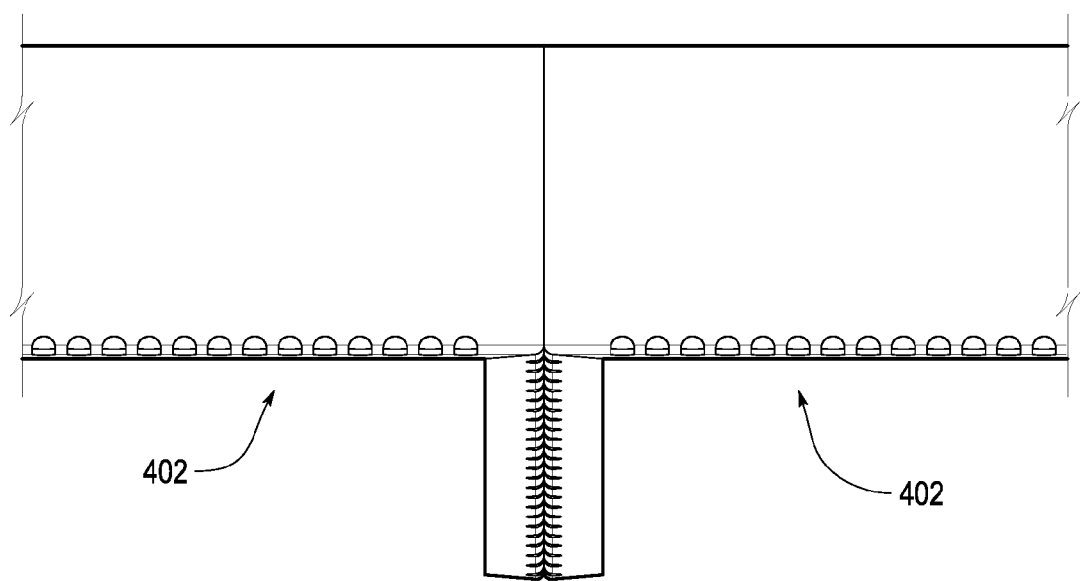
FIG. 24 is a plan view of portions of airframes, according to an embodiment of the present disclosure.

Various embodiments also allow single trade, single source responsibility of the system, instead of multiple trade, multiple source responsibility. In various embodiments, the airframe members 402, such as of adjacent modules, are mounted in abutting engagement as shown in FIG. 24.

Figure 25:
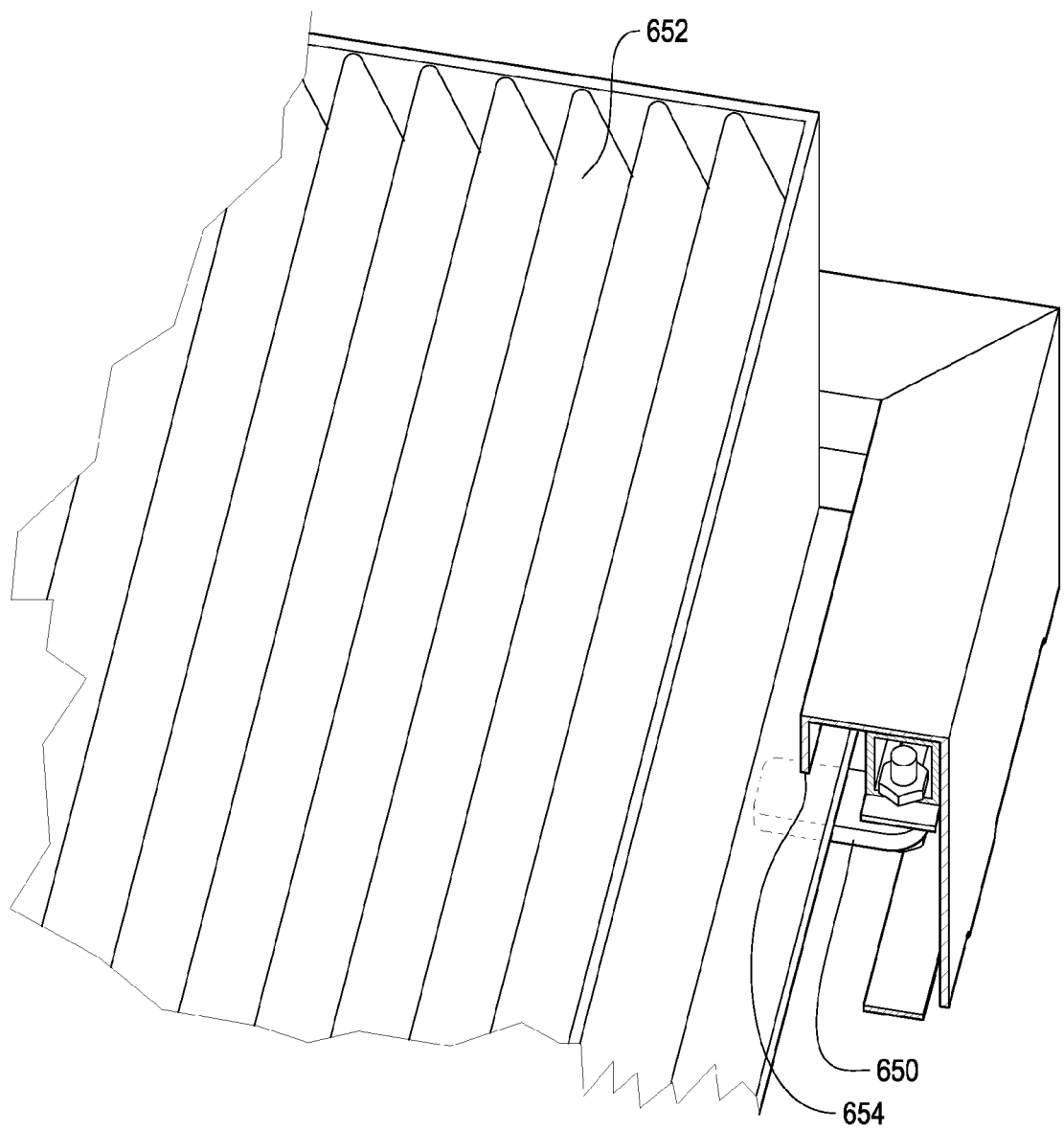
FIG. 25 is a perspective view of a module having a filter, according to an embodiment of the present disclosure.

As should be appreciated, the number and location of each of these modules may be varied as desired or needed, such as based on the particular application or environment. For example, a plurality of modules may be installed for a particular environment that includes easy load HEPA (see FIG. 25 showing a HEPA filter 652 locked into place with a HEPA lock 650 in combination with an airframe knife edge seal 654) and easy clean damper/diffuser features as described herein, such as using a hinged access configuration as described herein. Additionally, in some embodiments, single cell flex mount modules may be provided, which are configured like the structural mounts 610 and having bolt-on capabilities (e.g., bolt-on fastening or connection to another module, which allows for flexible and movable mounting locations and positions.

In various embodiments, multiple attachment points are provided per module (e.g., four attachment points per module). In these embodiments, anchoring installation time is reduced, which in some cases, is thirty times faster than conventional system installations.

Thus, as shown and described herein, various embodiments, including, for example, the supply air array 106 is configured to direct pressurized air underneath an entire lower surface of a frame structure that includes easily removable light assemblies. The pressurized air underneath the supply air array 106 reduces or eliminates turbulent recirculation of contaminants directly over the patient and surgical site. The air passages 450 direct air under the light housing 400 or any space between the airframe members 402. The pressurized air under the light housing 400 reduces or eliminates turbulent recirculation of air that might entrain contaminants.

Embodiments may be used in relation to a hospital operating room environment. Optionally, embodiments of the present disclosure may be used in various other settings in which pressurized airflow may be directed in combination with ceiling mounted equipment and/or lighting assemblies.

For example, embodiments of the present disclosure may be used in dental offices, manufacturing clean rooms, residential spaces, and the like. Additionally, it should also be appreciated that one or more air filtering, air sterilizing and/or air purifying devices or methods may be used in combination with each other, for example, in a multi-stage cleaning design to cleanse the air and/or surfaces through which the air passes.

For example, in various embodiments, the air cleansing device may be an air sterilizing device. The air sterilizing device may be any type of device that effects a sterilization of the air flow, which may include introducing or adding a cleansing or sterilizing agent or chemical into the air flow path. Thus, the air sterilizing device in various embodiments removes or changes the material properties of the contaminants or air particles to sterilize the air flow that is thereafter delivered as discussed herein. For example, the air sterilizing device may inject a cleansing or sterilizing agent or chemical into the air flow path that not only sterilizes or sanitizes the air, but also sterilizes or sanitizes the surfaces through which the air flows. It should be noted that any type of sterilizing or sanitizing method may be performed by the air sterilizing device, which in some embodiments may include using non-chemical methods to perform the sterilizing or sanitizing.

As another example, the air cleansing device may be an air purifying device. The air purifying device may be any type of device that purifies the air flow. Thus, the air purifying device in various embodiments changes the material properties of the contaminants or air particles to purify the air flow that is thereafter delivered as discussed herein. For example, the air purifying device may use one or more air ionization processes to purify the air flow, which can also effect a cleansing or purifying of the surfaces through which the air flows. It should be noted that any type of purifying method may be performed by the air purifying device, which in some embodiments may include using non-ionization methods to perform the sterilizing or sanitizing (e.g., different types of UV lights and catalysts).

It should be appreciated that any air purifying device may be used in or with one or more embodiments. For example, in one or more embodiments, any type of air purifying device that removes contaminants and sanitizes both the air and surfaces may be used. In some embodiments, the air purifying device is any device used to kill, render impotent or reduce bacteria, viruses, mold, fungi, allergens, VOCs, etc. Some examples of the air purifying device include, but are not limited to ultraviolet (UV) light, vaporized hydrogen peroxide (VHP), nano technology, ionization, bi-polar ionization, hydroxyl radicals, hydroperoxides, etc.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An air frame system comprising:
    a frame body defining one or more openings;
    a plurality of air passages along an inner periphery of the one or more openings;
    a light assembly removably coupled to the frame body outside of the one or more openings; and
    an air diffuser and a movable damper within the one or more openings, the air diffuser and the moveable damper hingedly mounted within the one or more openings to allow access within the one or more openings.

2. The air frame system of claim 1, further comprising an air filter within the one or more openings.

3. The air frame system of claim 2, wherein the air filter is removably lock fit in the one or more openings along a knife edge seal.

4. The air frame system of claim 1, further comprising a mounting arrangement having a coarse adjustment mounting arrangement defined by a first mounting plate and fine adjustment mounting arrangement defined by a second mounting plate.

5. The air frame system of claim 1, wherein the frame body comprises a plurality of different modular component types.

6. The air frame system of claim 1, wherein the frame body comprises a tube frame and a light housing coupled to the tube frame, the light housing configured to provide snap fit engagement with a light assembly.

7. An air frame system comprising:
plural air delivery mounting members, each having a rivet track and airflow openings configured to direct airflow therethrough, the air delivery mounting members defining one or more air frames and the rivet track comprising a longitudinally extending groove;
a lighting module coupled to the rivet tracks of the air delivery mounting members such that the lighting module is between air delivery mounting members; and
one or more structural mounts coupled to an outside portion of one or more air delivery mounting members such that the one or more structural mounts are located along a perimeter of an airfield.

8. The air frame system of claim 7, further comprising at least one or more lighting modules, one or more fire suppression modules or one or more audio/video modules, coupled to one or more of the delivery mounting members.

9. The air frame system of claim 7, wherein the air frame includes a filter lock at an inner wall.

10. The air frame system of claim 7, wherein the lighting module defines a light bar extending between adjacent air frames.

11. The air frame system of claim 7, wherein the one or more air frames include a removable filter element, removable though a hinged access, and a movable damper.

12. The air frame system of claim 7, further comprising a pressurized module defining a single point air source connection for the air frame system.

13. The air frame system of claim 7, wherein the lighting module includes a light cavity therein for receiving a lighting element, the light cavity having no mounting opening in walls thereof.

14. The air frame system of claim 7, wherein the lighting module includes only snap-fit elements without separate fastening members.

15. The air frame system of claim 7, wherein the airflow openings are configured to direct airflow therethrough and downward at angle to an underside of the lighting module to create laminar airflow directly to a surgical target zone that creates an airflow pressure to reduce or prevent turbulence.

16. The air frame system of claim 1, wherein the air diffuser and the moveable damper are hingedly mounted to a common hinge at a side within the one or more openings and configured to allow access from below the one or more openings into the one or more openings.

17. The air frame system of claim 7, wherein the rivet track is configured to receive therein an end of a rivet such that when the lighting module is coupled to the rivet tracks of the air delivery mounting members, the rivet does not penetrate into the air delivery mounting members.

* * * * *